United States Patent
Pourreau et al.

[11] Patent Number: 5,426,174
[45] Date of Patent: Jun. 20, 1995

[54] HYDROXY-FUNCTIONALIZED POLYOXYALKYLENE ETHER COMPOSITIONS DERIVED FROM MIXTURES OF $C_4$ EPOXIDES

[75] Inventors: Daniel B. Pourreau, Downingtown, Pa.; Thomas P. Farrell, Hockessin, Del.; Michael J. Cannarsa, West Chester, Pa.

[73] Assignee: ARCO Chemical Technology, L.P., Greenville, Del.

[21] Appl. No.: 258,623

[22] Filed: Jun. 10, 1994

Related U.S. Application Data

[63] Continuation-in-part of Ser. No. 986,812, Dec. 8, 1992, abandoned.

[51] Int. Cl.[6] .................. C07C 43/10; C07C 43/20; C08G 65/08
[52] U.S. Cl. ........................... 528/419; 528/413; 528/608; 528/618; 528/620; 528/622
[58] Field of Search ................ 528/419, 413; 568/608, 568/622, 618, 620

[56] References Cited

U.S. PATENT DOCUMENTS

| 2,841,479 | 7/1958 | Hefrer et al. | 44/58 |
| 3,321,412 | 5/1967 | Naro | 528/413 |
| 4,127,513 | 11/1978 | Bellis | 528/413 |
| 4,228,272 | 10/1980 | Del Pesco | 528/413 |
| 4,294,714 | 10/1981 | Lewis et al. | 252/34 |
| 4,393,199 | 7/1983 | Manser | 528/408 |
| 4,728,722 | 3/1988 | Mueller | 528/413 |

FOREIGN PATENT DOCUMENTS 854958 11/1960 United Kingdom.
WO90/15092 12/1990 WIPO.

OTHER PUBLICATIONS

Brzezinska. et al., *Makromol. Chem., Rapid Corman.* 7, 1–4 (1986).

Primary Examiner—John C. Bleutge
Assistant Examiner—D. R. Wilson
Attorney, Agent, or Firm—Stephen D. Harper

[57] ABSTRACT

Hydroxy-functionalized polyoxybutylene ether compositions having improved thermal and oxidative stability are prepared by the polymerization of a mixture of $C_4$ epoxides in the presence of an organic initiator containing hydroxy groups.

10 Claims, No Drawings

HYDROXY-FUNCTIONALIZED POLYOXYALKYLENE ETHER COMPOSITIONS DERIVED FROM MIXTURES OF C₄ EPOXIDES

This is a continuation-in-part of U.S. application Ser. No. 07/986,812, filed Dec. 8, 1992, now abandoned.

FIELD OF THE INVENTION

The present invention relates to hydroxy-functionalized polyoxyalkylene ether compositions prepared using a mixture of $C_4$ epoxides. Such compositions are useful as reactive intermediates in the preparation of fuel and lube oil additives, polyurethanes, and the like and have unexpectedly superior thermal stability as compared to homopolymers of the individual $C_4$ epoxides.

BACKGROUND OF THE INVENTION

Hydroxy-functionalized polyoxyalkylene ether compositions derived from ring-opening polymerization of epoxides have long been known to be materials which are directly useful as surfactants, functional fluids, and the like or which may be readily reacted further to provide polyurethanes, fuel additives, and the like. However, such compositions have generally been regarded as susceptible to thermal and/or oxidative degradation when exposed to high temperatures and air for prolonged periods of time. This lack of stability, which is particularly pronounced when the composition is prepared using an epoxide wherein at least one of the carbon atoms in the oxirane ring bears both a carbon and a hydrogen substitutent (as in propylene oxide, 1,2-butylene oxide, cis-2,3-butylene oxide, or trans-2,3-butylene oxide), has discouraged the use of such compositions in certain end-use applications requiring good thermal or oxidative resistance such as fuel detergent additives. Since the aforementioned epoxides which in theory could be used to manufacture compositions of this type are relatively inexpensive as compared to other polymerizable monomers, however, it would be highly desirable to develop hydroxy-functionalized polyoxyalkylene ether compositions based on such substituted epoxides which have improved heat- and/or air-tolerance.

SUMMARY OF THE INVENTION

This invention provides a hydroxy-functionalized polyoxybutylene ether composition obtainable as the addition polymerization product of a hydroxy group-containing organic initiator having from 1 to 8 hydroxy groups and a mixture of $C_4$ epoxides consisting essentially of 40 to 60 weight percent 1,2-butylene oxide, 10 to 30 weight percent cis-2,3-butylene oxide, and 20 to 40 weight percent trans-2,3-butylene oxide. The number of moles of $C_4$ epoxide incorporated into the hydroxy-functionalized polyoxybutylene ether composition is from 1 to 25 times the number of moles of hydroxy groups in the organic initiator. The $C_4$ epoxides are incorporated randomly in the composition. Such compositions have been found to possess a surprisingly high resistance to thermal and thermo-oxidative degradation.

DETAILED DESCRIPTION OF THE INVENTION

The hydroxy group-containing organic initiator is incorporated into the desired hydroxy-functionalized polyoxybutylene ether composition by ring-opening addition of the $C_4$ epoxides onto the initiator and may be any solid or liquid organic substance having a hydroxyl functionality of at least 1 and preferably no more than 8. Initiators having 1, 2, or 3 hydroxy groups per molecule are especially preferred for use. The hydroxy groups may be terminal or pendant, with secondary or primary hydroxy groups being most preferred. The hydroxy groups may be either aliphatic or aromatic in character (i.e., attached to either aliphatic or aromatic carbons). Illustrative examples of the types of initiators generally useful in preparing the compositions of this invention include, but are not limited to, monols, diols (including glycols), triols, tetrols, sugar alcohols, monosaccharides, disaccharides, alkyl glycosides, phenols, and the like.

One class of suitable hydroxy group-containing organic initiators includes those compounds corresponding to the general structure $R(OH)_n$ wherein R is an alkyl, aryl alkyl, or aryl radical and n is an integer of from 1 to 3. Examples of such initiators wherein R is an alkyl radical (linear, branched, or cyclic) include methanol, ethanol, isopropanol, 2-butanol, 1-octanol, octadecanol, 3-methyl-2-butanol, 5-propyl-3-hexanol, cyclohexanol, dodecanol, ethylene glycol, propylene glycol, 1,4-butanediol, 1,6-hexanediol, glycerin, 1,2,6-hexanetriol, trimethylol propane, 1,3-butanediol, 1,4-cyclohexanedimethanol, and the like. Illustrative examples of useful initiators wherein R is an aryl radical include phenol, resorcinol, catechol, 1-,2-, or 3-naphthol, 1,2-, 1,3-, 1,4-, 1,5-, 1,6-, 2,3-, 2,6-, or 2,7-dihydroxy naphthalene, 2,2'- or 4,4'-biphenol, and the like. Initiators wherein R is an aryl alkyl radical include, but are not limited to o-, m-, or p-cresol, bisphenol A, benzyl alcohol, methyl benzyl alcohol, bisphenol F, xylenol, thymol, and the like, as well as compounds having the general structure:

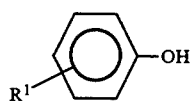

wherein $R^1$ is a $C_1$ to $C_{20}$ alkyl radical (e.g., nonyl phenol, phenol alkylated with propylene dimer, trimer, tetramer, or pentamer, octylphenol and other alkylated phenols, resorcinols, catechols, and the like). Alternatively, a polyoxyalkylene glycol having a number average molecular weight of from 106 to 500 may be utilized as the initiator including, for example, diethylene glycol, triethylene glycol, and other ethylene glycol oligomers, glycerol oligomers, dipropylene glycol, triethylene glycol, and other propylene glycol oligomers, ethoxylated, propoxylated, or butoxylated glycerin, trimethylolpropane, pentaerythritol, sorbitol, 2,3,4-trihydroxypentane, 1,2,6-trihydroxyhexane, alkyl phenols and the like, tetrahydrofuran oligomers, oxetane oligomers, and the like. The amount of hydroxy group-containing organic initiator to be utilized relative to the total amount of $C_4$ epoxide to be reacted is selected so as to provide the final polymerized product in the desired molecular weight.

The amount of epoxide utilized may be varied as desired. Typically, however, the number of moles of $C_4$ epoxide addition polymerized onto the hydroxy groups of the initiator is from 1 to 25 times the number of moles of hydroxy groups. Since quantitative conversion of the $C_4$ epoxide present in the reaction mixture is not always accomplished, it may therefore be necessary to utilize an excess of epoxide in order to attain the desired degree of $C_4$ epoxide incorporation into the hydroxy-functionalized polyoxybutylene ether product.

The mixture of $C_4$ epoxides incorporated into the compositions of this invention consists essentially of 40 to 60 (more preferably 45 to 55) weight percent 1,2-butylene oxide, 10 to 30 (more preferably, 15 to 25) weight percent cis-2,3-butylene oxide, and 20 to 40 (more preferably, 25 to 35) weight percent trans-2,3-butylene oxide. The use of a mixed $C_4$ epoxide feed stream of this type unexpectedly affords a hydroxy-functionalized polyoxybutylene ether composition having unique characteristics and properties as compared to the polymeric products obtained by homopolymerization of the separate component epoxides.

A low cost mixed $C_4$ epoxide feed stream suitable for use in the instant invention may be obtained by epoxidation of the mixed $C_4$ olefin stream available as a side stream from a commercial methyl tert-butyl ether (MTBE) process which is commonly referred to as "Raffinate-II". The mixed $C_4$ olefin stream may be subjected to epoxidation using conventional and well-known methods such as reaction with an active oxygen species such as an organic hydroperoxide or hydrogen peroxide and a transition metal catalyst such as molybdenum or titanium. The use of an acid-activated montmorillonite clay catalyst together with slow incremental addition of the $C_4$ epoxide mixture in order to produce the hydroxy-functionalized polyoxybutylene ether compositions of this invention is especially desirable. In such a process a mixture of the catalyst and the hydroxy group-containing organic initiator is formed. The $C_4$ epoxide mixture is then added incrementally to the mixture at a temperature of from 50° C. to 150° C. so as to accomplish ring-opening addition polymerization of the $C_4$ epoxides onto the hydroxy group-containing organic initiator to form the hydroxy-functionalized polyoxybutylene ether composition. The $C_4$ epoxide mixture is most preferably added at a rate such that the molar concentration of hydroxy groups in the mixture is maintained at a level greater than the molar concentration of $C_4$ epoxide in the mixture.

Advantages of the aforedescribed process include minimal formation of cyclic or unsaturated impurities, facile polymerization of the mixed epoxide feed so as to provide substantially random copolymerization and a largely homogeneous polymeric product (i.e., a polymeric product having minimal "block" character and which is a true copolymer rather than a physical mixture of homopolymers), and mild reaction conditions. In addition, the process uses a heterogeneous (insoluble) catalyst which may be readily recovered and recycled. Hydroxy-functionalized polyoxybutylene ether compositions having number average molecular weights of from about 300 to 5000 may be readily obtained using such a process.

Suitable acid-treated montmorillonite clays useful as catalysts in such a process include those synthetically-prepared or naturally-occurring clay minerals which have been contacted or washed with a strong acid and which are aluminum silicates or aluminum magnesium silicates. Such substances are the chief constituents of bentonite and fuller's earth and are often also referred to as smectites, bleaching earths, or bleaching clays. It is preferred that the montmorillonite clay be activated by treating with a mineral acid such as sulfuric acid, hydrochloric acid, phosphoric acid, or nitric acid. Methods of treating a montmorillonite clay with a relatively concentrated mineral acid solution which will yield catalysts suitable for use in the process of the invention are described in U.S. Pat. No. 4,127,513, the teachings of which are incorporated herein by reference. Alternatively, the montmorillonite clay may be acid-activated by treating with dilute (<15 weight percent) mineral acid solution and then drying the catalyst. The montmorillonite clay used is preferably substantially anhydrous and contains less than 3 weight percent water. U.S. Pat. No. 4,243,799, the teachings of which are incorporated herein by reference in their entirety, describes the preparation of substantially anhydrous montmorillonite clays which may be advantageously used. The preparation of another useful catalyst of this general type is taught in U.S. Pat. No. 4,228,272, incorporated herein by reference in its entirety. Certain acid-activated montmorillonite clays are also available commercially such as the material sold under the designation "K10" by Sud-Ehemie A.G.

The amount of acid-activated montmorillonite clay employed is not critical, although the rate of polymerization is somewhat dependent on the catalyst concentration. Sufficient clay should be utilized to effectively catalyze ring-opening polymerization of the $C_4$ epoxides to the desired level of conversion within a practically short period of time. Typically, the yield of product will tend to increase as the concentration of catalyst is increased. However, it has been found that the properties of the product obtained are not substantially affected by the quantity of catalyst utilized. Advantageous results are typically achieved if the clay is present in an amount of from 0.1 to 5 weight percent based on the total combined weight of epoxide and hydroxy group-containing organic initiator, although generally no more than 1 weight percent catalyst need be used. The acid-activated montmorillonite clay may be deployed, for example, in the form of a powder suspended in the reaction mixture or as pellets, beads of a monolith in a fixed catalyst bed. Although the clay is preferably dried prior to use, calcination usually is not desirable as a loss in catalyst activity tends to result.

The acid-activated montmorillonite clay and the hydroxy group-containing organic initiator are mixed prior to the introduction of the $C_4$ epoxide to the reaction mixture. Preferably, the resulting mixture is brought to the desired reaction temperature within the range of 50°-150° C. (more preferably, 50°-100° C.; most preferably, if minimization of unsaturation is desired, 60°-90° C.) before addition of the epoxide is begun.

The mixture of $C_4$ epoxides is most preferably added incrementally to the mixture of clay catalyst and organic initiator at a temperature of from 50° to 150° C. at a rate such that the molar concentration of hydroxy groups in the reaction mixture is maintained at a level greater than the molar concentration of $C_4$ epoxide in the mixture. The concentration of hydroxy groups may be readily determined either by standard wet chemical methods or by knowledge of the functionality and amount of the organic initiator employed, since the hydroxy groups present in the mixture are either on the initiator itself or are derived from the initiator hydroxy groups by ring-opening addition of epoxide. The concentration of unreacted $C_4$ epoxide during the reaction may be readily monitored by standard techniques such as gas chromatography and the rate of epoxide addition adjusted accordingly so as to keep the epoxide concentration below the hydroxy group concentration. The actual rate of addition needed to maintain the desired epoxide concentration may vary and will be dependent upon factors such as temperature, catalyst concentration and reactivity, initiator concentration and reactivity, epoxide reactivity, and so forth. Typically, however, the addition will be completed within a 0.5 to 20 hour time period, with the epoxide preferably being added in a substantially continuous manner. It is highly desirable to keep the hydroxy group concentration higher than the free $C_4$ epoxide concentration, and preferably at least twice the unreacted epoxide concentration, during the addition process in order to minimize the formation of cyclic and unsaturated by-products and to maximize the molecular weight and functionality of the hydroxy-functionalized polyoxybutylene ether composition. Adding the epoxide at ambient (20°–30° C.) temperatures is not desirable since there is an induction period before polymerization begins at such temperatures. This allows unreacted $C_4$ epoxide to accumulate and results in a rapid and substantial exotherm once polymerization is initiated. This has deleterious effects on the quality of the product thereby obtained.

After addition of the $C_4$ epoxide is completed, the resulting reaction mixture may be maintained at the same temperature or a different temperature until the desired level of epoxide conversion is achieved. Generally speaking, it will be desirable to attain at least 50% $C_4$ epoxide conversion, although conversions of 80% or better are possible.

As the $C_4$ epoxide is being added, it will be highly advantageous to provide good mixing of the reaction components so as to assure intimate contact on a molecular scale, minimize polydispersity (molecular weight distribution), provide better temperature control, and assure that epoxide and hydroxy group concentrations are uniform throughout the reaction mixture. When $C_4$ epoxide addition is completed, the resulting mixture may be permitted to continue reacting at a suitable temperature until the desired degree of $C_4$ epoxide conversion is achieved. The hydroxy-functionalized polyoxybutylene ether composition produced may be readily recovered and purified by separating the acid-activated montmorillonite clay catalyst from the other reaction mixture components by conventional means such as centrifugation, decantation, filtration, or the like. Any low molecular weight components such as solvent, unreacted epoxide, and the relatively minor amounts of cyclic by-products which may have been generated may be removed by distillation, preferably under vacuum. A wiped film evaporator is especially appropriate for this purpose. Any residual acidity may be neutralized by conventional means such as contacting with magnesium silicate or the like. One of the advantages of such a process is that the clay catalyst may be readily recovered and reused in subsequent runs or batches since it is not deactivated or otherwise chemically transformed, unlike other acidic polymerization catalysts which are predominantly soluble and which require neutralization with a base or washing with water to remove from the polymeric product. The unreacted $C_4$ epoxide which is recovered may similarly be recycled.

The process may be advantageously carried out in the presence of an organic solvent. Aromatic hydrocarbons (e.g., toluene, benzene, xylene, ethyl benzene), aliphatic hydrocarbons (e.g., hexane, cyclohexane), halogenated hydrocarbons (e.g., dichloromethane, chloroform, chlorobenzene) are generally suitable inert aprotic solvents. The use of a reactive solvent such as tetrahydrofuran which will copolymerize with the $C_4$ epoxides is also feasible. This is particularly advantageous wherein the organic initiator and the $C_4$ epoxide mixture are immiscible or insoluble in each other; THF may help to promote the formation of a single phase reaction mixture. It is desirable to conduct the process under anhydrous or substantially anhydrous conditions. When the reaction temperature is greater than the normal boiling point of the $C_4$ epoxide mixture being polymerized, a closed reaction vessel capable of withstanding pressures above atmospheric pressure may be utilized so as to keep the bulk of the epoxide in the liquid phase in contact with the clay catalyst and hydroxy group-containing organic initiator. In general, it has been found that the process may effectively be carried out at autogenous pressures.

The hydroxy-functionalized polyoxybutylene ether compositions of the invention have many uses, such as, for example, starting materials for the production of polyurethanes, antiredeposition agents, polyesters, lubricants, surfactants, viscosity index improvers, crude oil emulsion breakers, controlled release agents, synthetic fiber oiling agents, brake fluids, heat transfer media, lube oil additives, stabilizers, dispersants, and the like.

For example, deposit control additives of the type described in U.S. Pat. No. 4,294,714 (incorporated herein by reference in its entirety) may be readily prepared using the process of this invention. These additives are salts of $C_3$–$C_{30}$ organic monocarboxylic acids and hydrocarbyl poly(oxyalkylene) amino carbamates corresponding to the general structure

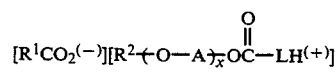

wherein:
(1) $R^1$ is a hydrocarbyl group having a carbon atom content in the range 3 to 30 (preferably 6 to 20) selected from the group consisting of alkyl, phenyl, cyclohexyl, alkenyl, cyclohexenyl, combinations thereof and of said groups having a single hydrogen atom thereof substituted by a hydroxyl of alkoxyl group, provided that said substituent is attached to a carbon atom at least 4, preferably 5, carbon atoms distant from the carboxyl group of said anion;
(2) $R^2$ is a hydrocarbyl group having a carbon atom content in the range from 1 to 30 selected from the group consisting of phenyl, mono-, di- and trialkylphenyl, alkyl, alkenyl, cyclohexyl, cyclohexenyl and combinations thereof;
(3) A is an alkylene group having a carbon atom content in the range of from 2 to 4 and x is an integer sufficient to provide said cation in unprotonated form with a molecular weight in the range of from about 500 to 10,000;
(4) L is monovalent and selected from the group consisting of radicals of the formula

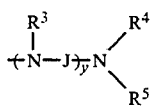

wherein J is an alkylene group having a carbon atom content in the range 2 to 6 and y is an integer in the range 1 to 11

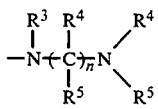

wherein n is an integer in the range 2 to 6, and -HNCH$_2$C(OH)HCH$_2$NH$_2$;

(5) R$^3$, R$^4$, R$^5$ are the same or different groups having a carbon atom content in the range 0 to 16 selected from the group consisting of hydrogen, hydrocarbyl, acyl, alkoxy, ketoalkyl, hydroxyalkyl and cyanoalkyl groups.

The compositions of this invention are especially useful for the production of the aforesaid deposit control additives wherein A represents butylene groups having the structures -CH$_2$CH(CH$_2$CH$_3$)-, -CH(CH$_2$CH$_3$)CH$_2$- and -CH(CH$_3$CH(CH$_3$)-(cis or trans).

From the foregoing description, one skilled in the art can readily ascertain the essential characteristics of this invention and, without departing from the spirit and scope thereof, can make various changes and modifications of the invention to adapt it to various usages, conditions, and embodiments.

The following examples further illustrate the invention, but are not limitative of the invention in any manner whatsoever.

EXAMPLE 1

This example demonstrates the use of a mixed C$_4$ epoxide feed stream obtained by epoxidation of "Raffinate II" and containing ca. 50 weight % 1,2-butylene oxide, 20 weight % cis-2,3-butylene oxide, and 30 weight % trans-2,3-butylene oxide. A 500 mL autoclave reactor was charged with nonyl phenol (15.0 wt. %), and oven-dried (120° C., 2 hr.) commercial montmorillonite clay "K10" purchased from Aldrich Chemical Company (0.3 wt. %). The autoclave reactor was sealed and the contents heated to 70° C. with stirring (500–1000 rpm). Using an ISCO pump, the mixed C$_4$ epoxide feed was added to the reactor over a 3 hour period. The resulting mixture was then stirred for another 2.3 hours. The reaction temperature ranged from 60° C. to 132° C.

The solution of hydroxy-functionalized polyoxyalkylene ether compound thereby obtained was filtered hot through two in-line metal filters (90 and 7 micron porosity) to remove the clay catalyst. The hot filtrate was collected in a 1000 mL hoke vessel, allowed to cool, and then transferred to a wiped-film evaporator. Unreacted epoxide, cyclics, and unreacted initiator, were removed in the wiped-film evaporator under vacuum. The hydroxy functionalized polyoxybutylene ether product obtained had the following characteristics:

| Epoxide conversion, % | 51 |
| Product selectivity, % | 100 |
| Product yield, % | 51 |
| $M_n$ | 338 |
| $M_w$ | 680 |
| $M_w/M_n$ | 2.01 |

EXAMPLE 2

The procedure of Example 1 was repeated using toluene as solvent and a propoxylated glycerin containing about 5 equivalents of propylene oxide per equivalent of glycerin (14.7 wt. %) as the initiator. Epoxide addition time was 3.0 hours, with a subsequent reaction time of 2.5 hours. Reaction temperature ranged from 60° C. to 124° C. during the course of the reaction. The hydroxy-functionalized polyoxybutylene ether composition obtained had the following characteristics:

| Epoxide conversion, % | 88 |
| Product yield, % | 83 |
| $M_n$ | 670 |
| $M_w$ | 930 |
| $M_w/M_n$ | 1.85 |

EXAMPLE 3

An appropriately sized autoclave reactor is charged with nonyl phenol (40 parts by weight), hexanes (50 parts by weight), and an acid-activated montmorillonite clay catalyst (1.8 parts by weight) prepared in accordance with Example 1 of U.S. Pat. No. 4,127,513. The contents of the reactor are heated to 75° C. and a mixture of C$_4$ epoxides derived from "Raffinate II" (324 parts by weight; 50 weight percent 1,2 butylene oxide, 20 weight percent cis-2,3-butylene oxide, and 30 weight percent trans-2,3-butylene oxide) added at a rate so as to maintain the molar concentration of hydroxy groups in the mixture at a level ca. twice the molar concentration of epoxide in the reaction mixture. When addition is completed, the reaction mixture is heated at 75° C. for another 10 hours. The butoxylated nonyl phenol product expected to be obtained may be converted into a useful deposit control fuel additive as described in U.S. Pat. No. 4,294,714.

EXAMPLES 4-7

A series of C$_4$ epoxide-derived hydroxy-functionalized polyoxybutylene ether compositions was prepared to demonstrate the advantages of incorporating a mixture of 1,2-butylene oxide, cis-2,3-butylene oxide, and trans-2,3-butylene oxide into such compositions. The compositions were prepared using a one liter autoclave reactor. The volume of epoxide(s) used in each example was 250 mL (except in the case of Example 7, where only 110 mL was used). The molar ratio of epoxide to hydroxy group-containing organic initiator (1-dodecanol; ca. 29.6 g) was 18.2:1 (for a theoretical molecular weight of ca. 1500). Heptane was used as a solvent (50 ml, except in Example 7 where 30 mL was present). Montmorillonite acid activated clay (K-10) was present at a 0.3 weight % level as catalyst.

The experimental procedure for each rtm was as follows: The initiator was charged to the reactor and the weight charged recorded. Heptane solvent was then charged, followed by catalyst, and the reactor sealed.

After purging and pressure testing with nitrogen, the reactor was heated with stirring to 70° C.

The epoxide or mixture of epoxides indicated in Table 1 was then added slowly from an ISCO pump. In all cases a 5 hour addition time (50 mL/hr pumping rate, except for Example 7 where a pumping rate of 22 mL/hr was used). During the epoxide addition, the internal temperature was kept between 70° C. and 74° C. by the application of cooling water through internal cooling coils.

After epoxide addition was completed, the contents of the reactor were heated to 90° C. over a 0.5 hr period, maintained at 90° C. for another hour, then cooled slowly to room temperature overnight. After removed from the reactor, the reactor mixture was vacuum filtered to remove the clay catalyst. Solvent and residual unreacted epoxide were removed with a wiped film evaporator. The hydroxyfunctionalized polyoxybutylene ether compositions thus obtained were analyzed by gel permeation chromatography and for hydroxy number and viscosity, as shown in Table 1.

The product obtained from each example was also tested by thermogravimetric analysis to determine its relative thermal and thermo-oxidative stability. Sample size ranged from 18 to 30 mg. The samples were subjected to a temperature ramp from 30° C. to 500° C. at a rate of 10° C. per minute. To measure thermal stability, nitrogen was used as the purge gas. To measure thermoxidative stability, air was used as the purge gas. Weight loss versus temperature was determined for each sample.

Example 5, which employed a mixture of $C_4$ epoxides in accordance with the present invention, yielded a composition having a higher molecular weight than any of the compositions obtained from a single $C_4$ epoxide. Fewer cyclic polyether by-products were produced. The Example 5 product exhibited a viscosity and hydroxy number similar to that observed for the Comparative Example 4 product (1,2-butylene oxide alone) and the Comparative Example 6 product (cis-2,3-butylene oxide alone), but markedly better than the corresponding properties of the comparative Example 7 product (trans-2,3-butylene oxide alone). All of the products (with the exception of the Comparative Example 7 product) formed 50 wt. % solutions with n-heptane. These solutions remained homogeneous even after one month at ambient temperature. The Comparative Example 7 product precipitated out of n-heptane solution at concentrations higher than 5 weight %.

Thermogravimetric analysis indicated that the Example 5 product, which was prepared using a mixture of $C_4$ epoxides, had significantly better thermal and thermo-oxidative stability than any of the Comparative Example products, which were each synthesized using a single $C_4$ epoxide. The onset of rapid decomposition for the Example 5 product was 71° to 99° C. higher in nitrogen and 33° to 65° C. higher in air than was observed for the Comparative Example products. This result was surprising, since the stability of a copolymer is ordinarily expected to be approximately the weighted average of the relative stabilities of the homopolymers of the individual comonomers present in the copolymer.

TABLE 1

| Example No. | $C_4$ Epoxide | MW, expected | $Mn^b$ | $Mw^b$ | Mw/Mn | Cyclics, % | Hydroxyl No., mg KOH/g | Viscosity c | Onset of Rapid Decomposition, °C. | |
|---|---|---|---|---|---|---|---|---|---|---|
| | | | | | | | | | $N_2$ | Air |
| 4* | 1,2-butylene oxide | 1492 | 621 | 856 | 1.38 | 7.5 | 139.1 | 40.2 | 218 | 225 |
| 5 | a | 1494 | 840 | 1124 | 1.34 | 3.0 | 84.3 | 40.1 | 311 | 276 |
| 6* | cis-2,3-butylene oxide | 1472 | 571 | 981 | 1.72 | 27.5 | 81.0 | 102 | 212 | 211 |
| 7* | trans-2,3-butylene oxide | 1559 | 661 | 876 | 1.32 | 1.0 | 184.6 | solid | 240 | 243 |

*Comparative example
a. 50% 1,2-butyleneoxide, 20% cis-2,3-butylene oxide, 30% trans-2,3-butylene oxide
b. GPC (uncorrected)
c. cps at 25° C.

We claim:

1. A hydroxy-functionalized polyoxybutylene ether composition obtainable as the addition polymerization product of a hydroxy group-containing organic initiator having from 1 to 8 hydroxy groups and a mixture of $C_4$ epoxides consisting essentially of 40 to 60 weight percent 1,2-butylene oxide, 10 to 30 weight percent cis-2,3-butylene oxide, and 20 to 40 weight percent trans-2,3-butylene oxide, wherein the number of moles of $C_4$ epoxide incorporated into the hydroxy-functionalized poly oxybutylene ether composition is from 1 to 25 times the number of moles of hydroxy groups in the organic initiator and the 1,2-butylene oxide, cis-2,3-butylene oxide, and trans-2,3-butylene oxide are incorporated randomly in the hydroxy-functionalized polyoxybutylene ether composition.

2. The composition of claim 1 wherein the organic initiator has the general structure

wherein R is an alkyl, aryl, or aryl alkyl radical and n is an integer of from 1 to 3.

3. The composition of claim 1 wherein the organic initiator has the general structure

wherein $R^1$ is a $C_1$ to $C_{20}$ alkyl radical.

4. The composition of claim 1 wherein the organic initiator has the general structure

wherein $R^2$ is a $C_1$ to $C_{20}$ alkyl group.

5. The composition of claim 1 having a number average molecular weight of from 300 to 5000.

6. The composition of claim 1 wherein the hydroxy group-containing organic initiator is an alkylphenol.

7. The composition of claim 1 wherein the mixture of $C_4$ epoxides consists essentially of 45 to 55 weight percent 1,2-butylene oxide, 15 to 25 weight percent cis-2,3-butylene oxide, and 25 to 35 weight percent trans-2,3-butylene oxide.

8. The composition of claim 1 wherein the hydroxy group-containing organic initiator has from 1 to 3 hydroxy groups.

9. The composition of claim 1 wherein the number of moles of $C_4$ epoxide is from 3 to 15 times the number of moles of hydroxy groups in the hydroxy group-containing organic initiator.

10. The composition of claim 1 wherein the organic initiator is an ethoxylated, propoxylated, or butoxylated alkylphenol.

* * * * *